United States Patent [19]
Wapner

[11] 4,331,144
[45] May 25, 1982

[54] BAND FOR SUPPORTING TRACHEOSTOMY TUBES OR THE LIKE

[75] Inventor: Herbert H. Wapner, Belmont, N.H.

[73] Assignee: Baka Manufacturing Company, Inc., Plainville, Mass.

[21] Appl. No.: 187,968

[22] Filed: Sep. 17, 1980

[51] Int. Cl.³ .............................................. A61M 25/02
[52] U.S. Cl. ...................... 128/207.17; 128/DIG. 15; 128/DIG. 26
[58] Field of Search ....................... 128/200.26, 207.17, 128/207.14, DIG. 15, DIG. 26, 207.11, 134

[56] References Cited

U.S. PATENT DOCUMENTS

| | | | |
|---|---|---|---|
| 1,592,345 | 7/1926 | Drager | 128/207.17 |
| 2,928,387 | 3/1960 | Layne | 128/207.11 |
| 3,086,529 | 4/1963 | Munz et al. | 128/134 |
| 3,535,719 | 10/1970 | Murcott | 128/DIG. 15 |
| 3,946,742 | 3/1976 | Eross | 128/207.17 |
| 4,027,666 | 6/1977 | Marx | 128/DIG. 15 |
| 4,088,136 | 5/1978 | Hasslinger et al. | 128/DIG. 26 |

Primary Examiner—Henry J. Recla
Attorney, Agent, or Firm—Wolf, Greenfield & Sacks

[57] ABSTRACT

A band for supporting a tracheostomy tube or the like comprising first and second straps each having a sponge-like inner surface adapted to lie against the skin and an outer layer of a looped material which functions as the female for Velcro-type fasteners. The straps are adjustably joined by a male Velcro-type patch on the back of one strap designed to engage the looped material on the face of the other strap. The free ends of the joined straps each carry a male Velcro-type fastener strip designed to thread through an opening in the flange of the tracheostomy tube to hold the tube in place.

2 Claims, 2 Drawing Figures

BAND FOR SUPPORTING TRACHEOSTOMY TUBES OR THE LIKE

INTRODUCTION

This invention relates to supports for tracheostomy tubes, endotracheal tubes and other medical appliances. More particularly, the invention relates to a low cost disposable band for the purpose recited, which can quickly be attached and detached from the appliance.

At the present time, tracheostomy tubes and endotracheal tubes are customarily supported in place by thin cotton tape which extends about the neck or head of the patient, and the ends of the tape tie to openings in the flanges of the tube. The cloth tape, which is very lightweight and flimsy has a tendency to curl and form a rope-like strap, which irritates the skin. Moreover, they are inconvenient to use because they do not have special fasteners for securing the ends of the cotton tape to the tube flanges. Rather, the tape ends are knotted about the flanges, which leave loose tape ends that may be annoying to the patient. And the knots, unless very carefully tied, may accidentally open and release the tube flanges.

The principal object of this invention is to provide a band which is comfortable to the patient and which is very easy for the nurse or other attendant to manipulate in order to attach the band to the flange of the tube.

Another important object of this invention is to provide a band suitable for supporting a tracheostomy or endotracheal tube, which has some flexibility and which is widely adjustable to accommodate patients and tubes of different size.

A more specific object of this invention is to provide a band suitable for attachment to a tracheostomy or endotracheal tube, which has sufficient body and integrity so that it will not curl or bind on the patient's neck or head and will not shread or come apart.

To accomplish these and other objects, the band of this invention includes a pair of straps each made of a very soft material such as a sponge-like foam sheet that is adapted to lie against the skin. The sheets have outer layers of a soft looped material. One of the straps also includes a short length of elastic webbing to provide some stretchability for the strap. A patch of male Velcro-type material is sewn to the back of the elastic webbing, and that patch is designed to latch onto the soft looped material on the face of the other strap to join the two straps together. The small patch of Velcro on the webbing allows band defined by the combined length of the two straps, to be readily adjusted to accommodate the patient. The outer ends of the band each carries a narrow male Velcro-type fastener strip that is designed to be threaded through an opening in the flange of the tracheostomy or endotracheal tube which it is to support, and turn back upon itself over the looped material of the strap so that it may be securely fastened in place. In this manner the band composed of the two straps holds the tube securely in place.

These and other objects and features of the present invention will be better understood and appreciated from the following detailed description of one embodiment thereof, selected for purposes of illustration and shown in the accompanying drawing.

BRIEF FIGURE DESCRIPTION

DETAILED DESCRIPTION

Figure 1:
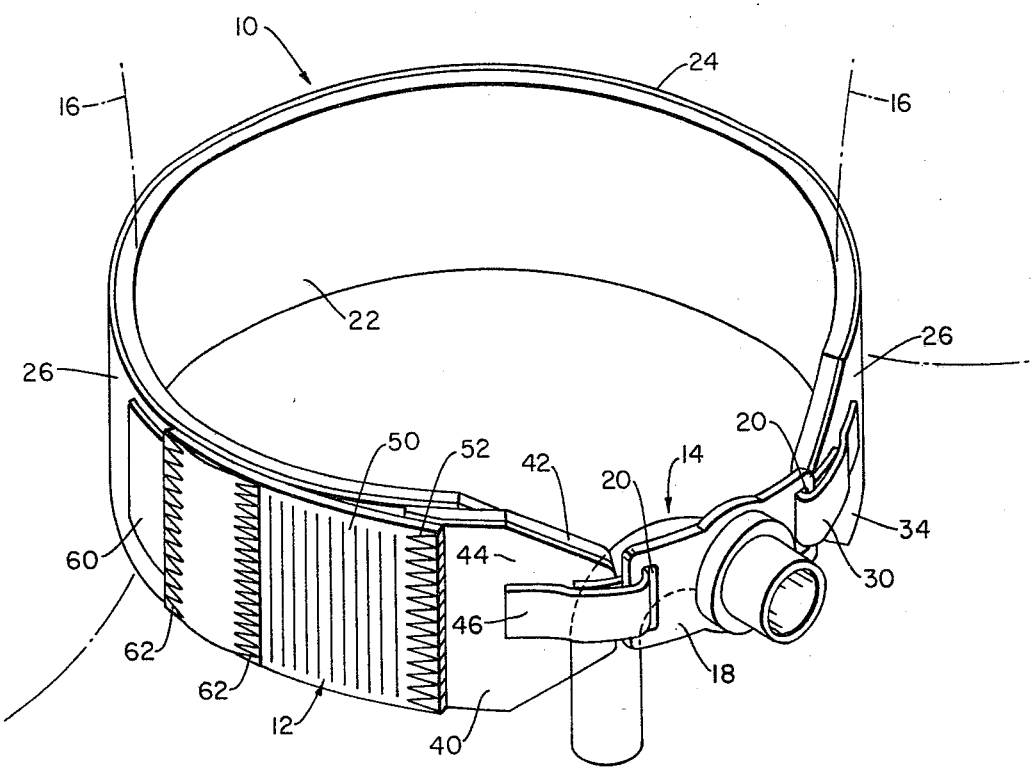
FIG. 1 is a perspective view of a band constructed in accordance with this invention shown supporting a tracheostomy tube on the neck of a patient.
Figure 2:
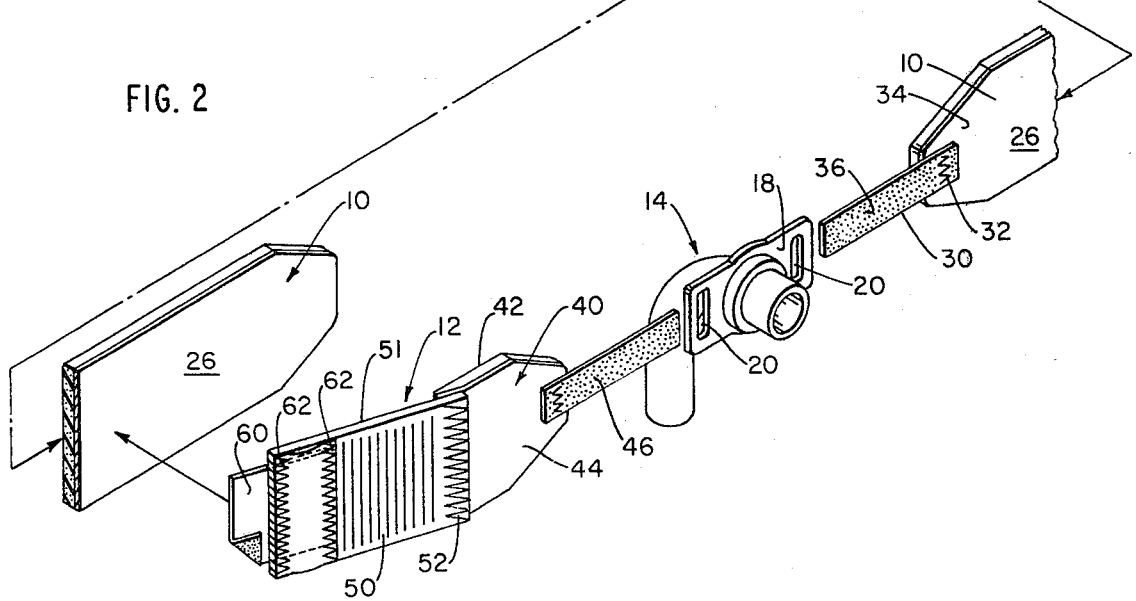
FIG. 2 is a fragmentary exploded view of the band and tracheostomy tube of FIG. 1 and illustrating how the various parts of the band are joined together and to the tube.

The band shown in FIGS. 1 and 2 is composed of two straps 10 and 12, which are releasably joined together when the band is in use as shown in FIG. 1, to support an appliance such as the tracheostomy tube 14. In FIG. 1 the assembled band is shown connected to the tube 14, and the broken lines 16 are intended to suggest the neck of a patient. The tracheostomy tube shown is obviously representative of a variety of different tracheostomy tubes. The tube itself is typically made of a PVC material and carries a thin, flexible and fixed flange 18 having opposed openings 20 to enable some form of band to be attached to it so as to support the tube in place.

The strap which may be considered the primary strap of the assembly because of its greater length is made of two layers of material with the inner or back ply 22 being a sponge-like non-stretchable substance which is very soft and flexible so that it will lie comfortably against the skin of the patient. Typically, it may be one-eighth inch in thickness and 1½ inches wide so that it is self-supporting and will not curl or roll and bind on the patient. The outer layer 24 of band 10 is composed of an inexpensive non-stretchable fabric made of a looped material typically woven of cotton of the velvet type, and the loops extend outwardly from the outer face 26 of strap 10 to serve as the female for a Velcro-type fastener, which will be described presently. Band strap 10 may, of course, be of a wide variety of lengths depending upon whether it is intended to be used by a large adult, very small child, or a person of some intermediate size.

A narrow strip 30 of male Velcro-type material is stitched as suggested at 32 to the end 34 of the primary strap, with the hook surface 36 facing forward or away from the surface 26 of the outer layer 24 of strap 10 when the strip is extended as in FIG. 2. As shown in FIG. 1, strip 30 is sized so that it may be threaded through the opening 20 of the flange 18 of tracheostomy tube 14 from the back side of the flange and be drawn over itself so that the hooks on surface 36 face the looped fabric on surface 26 of the primary strap and releasably lock to the surface and thereby form a closed ring loop which securely engages the flange.

Secondary strap 12 includes a short section 40 which is made of the same two materials as the primary strap 10, that is, a sponge-like backing layer 42 and an outer layer 44 made of a looped material. A thin male Velcro-type strip 46 is stitched to the end of the section 40 in the same manner that strip 36 is secured to the end 34 of the primary strap, and the strip 46 is designed to be threaded through the opening 20 on the left side of flange 18 in precisely the same manner as described in connection with the other strip so as to firmly hold the tube in place.

Secondary strap 12 includes a second section made of an elastic webbing 50 with a soft backing 51, which is stitched to the face of section 40 as suggested at 52. The elastic webbing is stretchable, although because it is of a very short length, it does not provide a great deal of stretch to the secondary strap. Rather, it is just sufficient to enable the attendant applying the band to select a comfortable pressure for the attachment of the band to the patient.

A patch of male Velcro-type material 60 is stitched to the inner face of the webbing 50 as suggested at 62, and the patch 60 is designed to engage the face 26 of the primary strap so as to close the loop of the band when the band is applied to the neck or about the head of the patient. Because the patch 60 may be attached any place along the surface 26 of the primary band, it is evident that it provides a great deal of adjustability for the band.

When the device is used, the attendant ordinarily connects the strip 30 of the primary strap 10 to one side of the flange of the tube and then places the strap underneath the neck or head of the patient. Next, the attendant applies the secondary strap to the other side of the flange of the tube. Thereafter, the attendant may gently press the patch 60 of the secondary strap against the surface 26 of the primary strap, which completes the task of securing the tube in place. It will be appreciated that the two narrow Velcro strips 30 and 46 may very conveniently be threaded through the openings in the tube flange, and they provide a secure attachment for the flange and they will not accidentally open. The attendant is not required to carefully knot tape or other material as is required with the conventional cotton tape now used. The elastic webbing 50 enables the attendant to attach the band with some tension if desired. But the yieldability of the webbing dos not interfere with expansion or other motion of the neck.

Having described the invention in detail, those skilled in the art will appreciate that modifications may be made of the invention without departing from its spirit. Therefore, it is not intended that the scope of the invention be limited to the specific embodiment illustrated and described. Rather, it is intended that the scope of this invention be determined by the appended claims and their equivalents.

What is claimed is:

1. A band intended to encircle the neck or head and support tracheostomy or endotracheal tubes or the like having flanges with openings to which the band may be secured comprising a primary strap made of non-stretchable material and having a soft sponge-like inner layer intended to lie against the skin when the band encircles the neck or head and an outer layer of looped material with the loops extending out of the face of the strap, a narrow, first, male, Velcro-type fastener permanently secured at one end to an end of the outer face of the outer layer of the strap with its hooked surface facing away from the strap and adapted to be threaded through an opening on a flange of the tube and be turned over so that the hooks beyond the opening may be pressed against the loops and lock onto them so as to retain the flange, a short secondary strap having a first portion thereof made of elastic webbing with a soft backing material, and a second portion which forms an extension of the first portion and made of the same material as the primary strap, a second, narrow, male, Velcro-type fastener permanently secured to the free end of the second portion of the secondary strap in the same manner that the first fastener is secured to the first strap so that it can be threaded through an opening in the flange of the tube to retain the flange, and a male Velcro-type coupling on the back of the webbing material adjacent its free end with the hooks facing rearwardly on the webbing so that it may releasably lock onto the front face of primary strap so that the band may comfortably encircle the neck or head and have an adjustable length.

2. A band intended to encircle the neck or head for supporting tracheostomy or endotracheal tubes or the like having flanges with openings to which a band may be secured comprising a primary strap having a soft rear surface to lie against the skin when the band encircles the neck or head and an outer layer of looped material with the loops extending out of the face of the strap, a first, male, Velcro-type fastener secured adjacent one end of the primary strap and adapted to be threaded through an opening in the tube flange and lock onto the outer surface of the primary strap, a secondary strap having an outer layer of looped material with the loops extending out the face, a second, male, Velcro-type fastener secured adjacent one end of the secondary strap and adapted to be threaded through another opening in the tube flange and lock onto the outer surface of the secondary strap, fastening means carried by the secondary strap for engaging the primary strap to releasably secure the two straps together and adjust their effective combined length, said fastening means being a Velcro-type patch sewn to the rear surface of the secondary strap for engaging the loops on the face of the primary strap, and wherein at least a portion of one of said straps being stretchable.

* * * * *